US010117783B2

(12) United States Patent
Cotton et al.

(10) Patent No.: US 10,117,783 B2
(45) Date of Patent: Nov. 6, 2018

(54) WOUND DRESSING

(75) Inventors: Stephen Michael Cotton, Paplewick (GB); Bryony Jayne Lee, Deeside (GB)

(73) Assignee: CONVATEC Technologies Inc., Las Vegas, NV (US)

( * ) Notice: Subject to any disclaimer, the term of this patent is extended or adjusted under 35 U.S.C. 154(b) by 0 days.

(21) Appl. No.: 13/120,733

(22) PCT Filed: Sep. 29, 2009

(86) PCT No.: PCT/GB2009/002342
§ 371 (c)(1),
(2), (4) Date: Aug. 8, 2011

(87) PCT Pub. No.: WO2010/035017
PCT Pub. Date: Apr. 1, 2010

(65) Prior Publication Data
US 2012/0130332 A1    May 24, 2012

(30) Foreign Application Priority Data

Sep. 29, 2009 (GB) .................... 0817796.6

(51) Int. Cl.
| A61F 13/51 | (2006.01) |
| A61L 15/22 | (2006.01) |
| D06B 1/00 | (2006.01) |
| G01N 27/24 | (2006.01) |
| A61F 13/02 | (2006.01) |
| A61F 13/00 | (2006.01) |

(52) U.S. Cl.
CPC ........ A61F 13/0203 (2013.01); *A61F 2013/00753* (2013.01)

(58) Field of Classification Search
CPC ............ A61F 13/51; A61L 15/22; D06B 1/00
See application file for complete search history.

(56) References Cited

U.S. PATENT DOCUMENTS

| 4,773,238 | A | * | 9/1988 | Zafiroglu ................. D04H 1/52 66/192 |
| 4,891,957 | A | | 1/1990 | Strack et al. |
| 4,957,795 | A | * | 9/1990 | Riedel .............................. 428/74 |
| 5,647,842 | A | | 7/1997 | Kininmonth et al. |
| 6,233,795 | B1 | * | 5/2001 | Dischler ................ D06C 11/00 26/28 |

(Continued)

FOREIGN PATENT DOCUMENTS

| EP | 0 092 999 | 11/1983 |
| EP | 0 130 061 | 1/1985 |

(Continued)

OTHER PUBLICATIONS

White, Sarah E. "Yarn Over". About Home. <http://knitting.about.com/od/knittingglossary/g/yarn_over.htm>. Oct. 29 2007.*

(Continued)

*Primary Examiner* — Tatyana Zalukaeva
*Assistant Examiner* — Sara Sass
(74) *Attorney, Agent, or Firm* — Wilson Sonsini Goodrich & Rosati

(57) ABSTRACT

A wound dressing comprising an absorbent layer, the absorbent layer being gathered in a longitudinal direction by one or more resilient yarns.

8 Claims, 2 Drawing Sheets

(56) References Cited

U.S. PATENT DOCUMENTS

Figure 1:
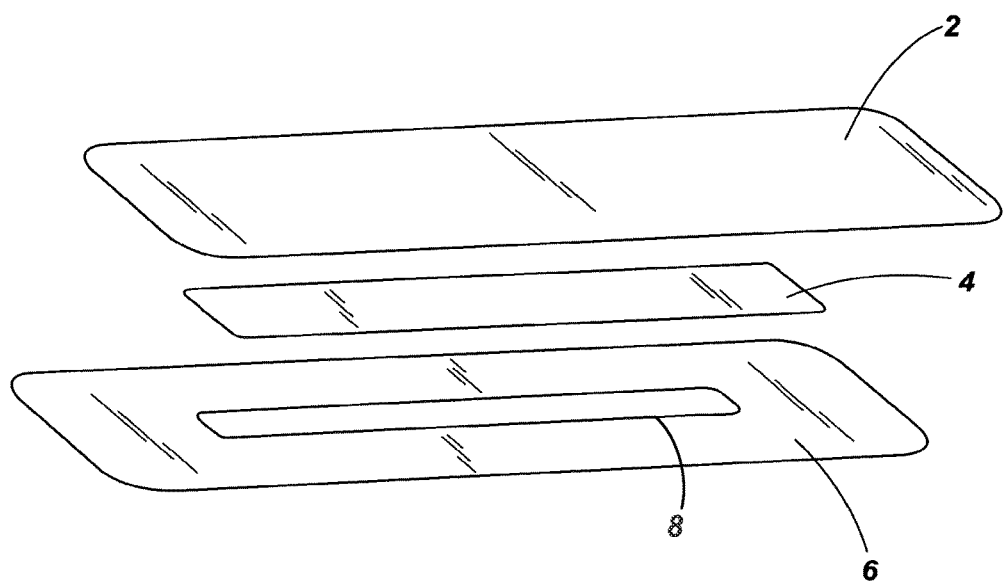

| | | |
|---|---|---|
| 6,267,744 B1* | 7/2001 | Roberts et al. .................. 602/76 |
| 2003/0040691 A1 | 2/2003 | Griesbach et al. |
| 2005/0015068 A1 | 1/2005 | Bean et al. |
| 2006/0089614 A1* | 4/2006 | Bonnin .................... 604/385.27 |
| 2006/0127462 A1* | 6/2006 | Canada et al. ................. 424/445 |
| 2007/0042024 A1* | 2/2007 | Gladman et al. ............. 424/445 |
| 2007/0160654 A1* | 7/2007 | Ferguson ...................... 424/445 |
| 2007/0173162 A1* | 7/2007 | Ethiopia et al. .............. 442/327 |
| 2007/0225663 A1* | 9/2007 | Watt et al. .................... 604/313 |

FOREIGN PATENT DOCUMENTS

| | | |
|---|---|---|
| GB | 738 722 | 10/1955 |
| WO | WO 93/12275 | 3/1993 |
| WO | WO 94/16746 | 8/1994 |
| WO | Wo 2007/003905 | 1/2007 |

OTHER PUBLICATIONS

Worst, Edward. "Problems in Raffia". Industrial Education. vol. 8. CCM Professional Magazines, Inc. 1919. p. 183.*

The Jubilee Method: a modern dressing design which reduces complications and is cost-effective following total knee and hip arthroplasty. Dillon J.M., Clarke, J.V. et al Dept of Orthopaedics, Golden Jubilee National Hospital Glasgow EWMA2007, Glasgow.

* cited by examiner

WOUND DRESSING

This invention relates to a wound dressing, in particular to wound dressings for use on post surgical sites. The invention preferably relates to dressings comprising gel forming fibres used on sites requiring a high degree of conformability and resilience such as those on the hip or knee following orthopaedic surgery.

Wounds on post operative sites such as those following knee or hip surgery can suffer problems with blistering of the skin around the incision site and infection. In addition frequent dressing changes may be necessary due to copious discharge produced at the site.

It is known to use carboxymethylated cellulosic materials in situations where a high degree of exudate absorption is required. For example, WO 93/12275 describes the production of various absorbent products capable of absorbing many times their own weight of water. This causes the carboxymethylated fibres to form a gel. WO 94/16746 and WO 00/01425 describe the use of carboxymethylated Lyocell materials in wound dressings where the advantages of gel formation in preventing adherence and therefore reducing wound damage and pain on removal are discussed.

It is also known to use carboxymethylated cellulosic fibres in the form of a fabric in combination with an adhesive layer to treat post surgical sites. For example, it is known to use Aquacel® (a dressing made of carboxymethylated cellulosic fibres and sold by ConvaTec) combined with Duoderm® Extra Thin® (an occlusive exterior layer which is also adhesive) on post surgical sites in a method reported as the Jubilee method where an Aquacel island in the form of a narrow strip is surrounded at its periphery with an overlying layer of Duoderm Extra Thin which secures the dressing to the site (The Jubilee Method: a modern dressing design which reduces complications and is cost-effective following total knee and hip arthroplasty. Dillon J. M., Clarke, J. V. et al. Dept of Orthopaedics, Golden Jubilee National Hospital Glasgow EWMA2007, Glasgow).

Although such a combination of advanced dressing materials provides advances over a traditional gauze dressing in that for instance blistering and infection are reduced, post surgical sites have specific needs that remain to be addressed. For instance, dressings for use on the knee or hip following arthroplasty or those on sites where there is a wide range of patient movement require high conformability and resilience from the dressing otherwise patient movement is restricted and blistering occurs due to friction between the dressing and the skin. Most absorbent pads are unable to stretch and so delaminate on flexion of the knee or joint. Even gel-forming dressings break down with repeated movement of the limb. The non-woven fabric of Aquacel, although conformable and flexible can tend to shrink on absorption of exudate making it less able to bend and stretch. It would be desirable to bring the advantages of gel forming dressings to surgical sites by having the dressings available in a form with a reduced tendency to shrink and an ability for all the layers to stretch and recover so that the dressing accommodates the normal movement of the joint during wear.

It is known to increase the tensile strength of bandages by stitching the bandage longitudinally with one or more lines of stitches. WO 2007/003905 describes such dressings which are particularly suitable for use in dressing burns.

We have found that it is possible to improve the resilience of dressings to mitigate the problems associated with dressing post operative sites where movement occurs.

Accordingly the invention provides a wound dressing comprising an absorbent layer, the absorbent layer being gathered in a longitudinal direction by one or more resilient yarns.

By resilient is meant that the yarn or thread is able to extend and contract to its former shape. The gathers in the absorbent layer formed by the resilient thread or yarn, enable the absorbent layer to extend and contract with movement so that when, for example, the patient's leg is bent the dressing stretches and when the leg is straightened, the dressing recovers its former size. This resilience means that the absorbent layer maintains close conformability with the wound during movement of the patient. It also means that the dressing has a reduced tendency to delaminate during wear. Having the ability to stretch means that there is less movement between the dressing and the patient which reduces blistering.

Preferably the dressing further comprises an adhesive layer overlying the absorbent layer on a surface furthest from the wound in use and extending beyond the periphery of the absorbent layer so as to secure the dressing to the skin.

Preferably the absorbent layer further comprises lines of longitudinal warp stitches formed from an inelastic thread which stitching is longitudinal in that it is generally parallel to the long dimension of the absorbent layer. The warp stitches are preferably made in the absorbent layer after it has been formed.

The inelastic warp stitching preferably passes through the whole thickness of the absorbent layer and is visible on both sides. The absorbent layer preferably comprises two or more layers of fabric that are layered together and stitch bonded with lines of longitudinal inelastic warp stitches. The resilient thread is preferably woven in between the stitches of the inelastic warp stitching and in between the sheets of fabric. By having two layers of fabric it is possible to hold the resilient thread or yarn out of direct contact with the wound.

The resilient thread gathers the absorbent layer and enables it to elongate and then return to shape. The resilient thread can be stitched through the absorbent layer to gather the dressing or woven through a separate line of inelastic warp stitches. The resilient thread can be stitched through the absorbent layer in lines of longitudinal stitches 1 mm to 10 mm apart, more preferably 2 mm to 5 mm apart. The resilient thread is preferably applied to the absorbent layer after the absorbent layer has been formed.

The absorbent layer preferably has an absorbency of at least 2 grams of 0.9% saline solution per gram of fabric as measured by the free swell method. The absorbent layer preferably comprises gel forming fibres. By gel forming is meant hygroscopic fibres which upon the uptake of wound exudate become moist slippery or gelatinous and thus reduce the tendency for the surrounding fibres to adhere to the wound. The gel forming fibres can be of the type which retain their structural integrity on absorbtion of exudate or can be of the type which lose their fibrous form and become a structureless gel. The gel forming fibres are preferably spun sodium carboxymethylcellulose fibres, chemically modified cellulosic fibres, pectin fibres, alginate fibres, chitosan fibres, hyaluronic acid fibres, or other polysaccharide fibres or fibres derived from gums. The cellulosic fibres preferably have a degree of substitution of at least 0.05 carboxymethyl groups per glucose unit. The gel forming fibres preferably have an absorbency of at least 2 grams 0.9% saline solution per gram of fibre (as measured by the free swell method).

Preferably the gel forming fibres have an absorbency of at least 10 g/g as measured in the free swell absorbency method, more preferably, between 15 g/g and 25 g/g.

Carboxymethylation can be achieved, for example, by sequential or simultaneous treatment of the cellulosic material with a strong alkali, such as aqueous sodium hydroxide, and monochloroacetic acid or a salt thereof. The appropriate reaction conditions will depend upon the composition of the fabric and the degree of carboxymethylation required and will be readily apparent to the person skilled in the art. They may be identical or similar to those described in WO 93/12275, WO 94/16746 or WO 00/01425 to which the reader is directed for further detail.

Desirably the carboxymethylation is carried out in the presence of industrial methylated spirits (IMS), and IMS is preferably also used in a subsequent washing step, suitably along with water, as a cleaner and steriliser. The degree of carboxymethylation is desirably such that upon absorption of exudate the fibres at the skin-contacting surface of the bandage form a gel.

The dressing may for instance comprise non gel forming fibres and in particular may comprise Linel, lycra or other elastic fibre.

The dressing may be in the form of a rectangle and be available in the following sizes, 9 cm×10 cm, 9 cm×15 cm, 9 cm×25 cm, 9 cm×35 cm.

The lines of inelastic warp stitching may be from 1 mm to 10 mm apart and preferably from 2 mm to 5 mm apart. The lines of inelastic stitching are typically crocheted or knitted and have the appearance of a chain stitch but other stitch patterns may also be used. Preferably, the lines of resilient stitching gather the absorbent layer so that the absorbent layer is able to elongate by 25% to 85%, more preferably 35% to 75% and most preferably 40% to 70% and then recover even when the absorbent layer is hydrated. More preferably, the lines of warp stitching are made in a yarn or thread such as nylon or polyester or Tencel or any thread which is strong and easily processed. The resilient stitches are made in a resilient yarn such as an elastomeric yarn or linel or lycra or yarn which has good stretch and recovery or an elastane yarn which is an elastomeric yarn with greater than 85% polyurethane such as linel or Lycra or Spandex.

The dressing may comprise a further adhesive layer overlying the first adhesive layer but on the opposite side of the absorbent layer. Preferably the adhesive layer includes a reinforcing scrim of polyurethane film to reduce any tendency of the adhesive to delaminate on dressing removal. The further adhesive layer preferably has a window cut from it that coincides with the absorbent layer and is present to hold the absorbent layer within the dressing and enable direct contact between the absorbent layer and the wound.

The adhesive layer may be of the type comprising a homogenous blend of one or more water soluble hydrocolloids and one or more low molecular weight polyisobutylenes such as are described in EP-B-92999 incorporated herein by reference. The water soluble hydrocolloids may be selected from sodium carboxymethylcellulose, pectin, gelatine, guar gum, locust bean gum, karaya gum, and mixtures thereof. The polyisobutylenes may be selected from low molecular weight polyisobutylenes having a viscosity average molecular weight of from 36,000 to 58,000 (Florey). The adhesive layer is capable of absorbing exudate while maintaining adhesion of the dressing to the skin.

Alternatively the adhesive composition may comprise a homogeneous blend of one or more hydrocolloids, one or more low molecular weight polyisobutylenes, one or more styrene block copolymers, mineral oil, butyl rubber, a tackifier and small amounts of optional components. By selection of specific ranges of the amounts of the above listed components, an adhesive composition may be prepared having good adhesion to the skin and stretchability. Such compositions and the preparation therefore are disclosed in EP-B-130061.

Preferably the adhesive is such that the removal of an adhesive wound dressing is not traumatic to the patient. Preferably the adhesive ensures a secure application of the dressing whist still permitting non-traumatic removal. Non-traumatic dressing removal may be facilitated by using an adhesive which gels slightly upon interaction with a fluid. The gel formation aiding dressing removal.

The absorbent layer may comprise one or more medicaments. For example an antimicrobial agent, or an antibiotic, or an anaesthetic on an anti-inflammatory agent or a skin protective agent or an odour absorbing agent.

In a further aspect the invention provides a method of manufacturing a wound dressing for use on post surgical wounds characterised in that the method comprises the steps of:

(i) forming an absorbent layer; and
(ii) gathering the absorbent layer with a resilient yarn.

Preferably the absorbent layer is formed first and is then stitched with a resilient yarn to gather it. The absorbent layer is preferably a layer of non woven gel forming fibres which is first formed and then stitch bonded with an inelastic yarn and a resilient yarn to gather it.

Figure 2:
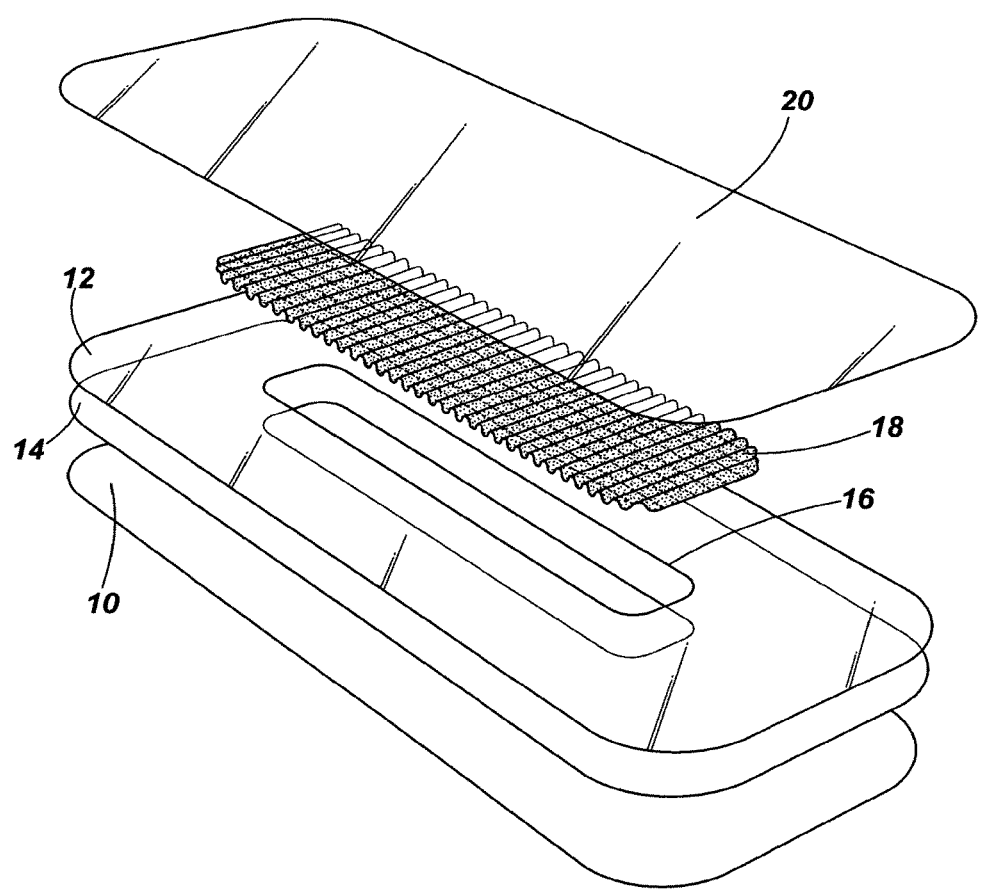

Preferred embodiments of the invention will now be described with reference to the accompanying drawings in which:

FIG. 1 is a view of a preferred embodiment of the dressing according to the invention in perspective view; and FIG. 2 is an exploded view of a further embodiment of the dressing according to the invention in perspective.

In FIG. 1 the dressing comprises a layer of hydrocolloid adhesive 2 onto which is bonded an absorbent layer 4. A further layer 6 of hydrocolloid adhesive having a window 8 is applied over the absorbent layer so that the absorbent layer is sandwiched between the two adhesive layers with the window exposing the absorbent layer to the surgical site.

The absorbent layer is made from a non woven roll made by forming a web of Lyocell which is then hydroentangled. The web is then carboxymethylated by sequential or simultaneous treatment of the cellulosic material with a strong alkali, monochloroacetic acid or a salt thereof. Two webs of the resulting fabric are then fed into a stitch bonding machine and stitched simultaneously with lines of longitudinal stitching in an inelastic yarn and a resilient yarn woven in between the stitches and so secured at the centre of the webs. The resilient yarn gathers the absorbent layer (not shown) and is carried by the inelastic stitch bonded yarn. The resulting layer has a basis weight of 350 gm$^{-2}$.

In FIG. 2 the dressing comprises two layers of hydrocolloid adhesive 10, 12 reinforced by a polyurethane film 14 into which is cut a window 16. An absorbent layer 18 is positioned over the window and overlaps the adhesive layer around its margin. A further layer 20 of adhesive backed with a polyurethane film is applied over the absorbent layer so that the absorbent layer is sandwiched between the layers with the window 16 exposing the absorbent layer 18 to the surgical site.

The absorbent layer is made from a tow of carboxymethyl cellulose filaments which has been needlefelted. Two webs of the needlefelted tow are fed into a stitch bonding machine and stitched simultaneously with lines of longitudinal stitching as shown in FIG. 2 in inelastic yarn and with a resilient yarn woven inbetween the stitches and so secured at the centre of the webs.

In the context of the present invention the terms yarn and thread are used to interchangeably.

Preferred embodiments of the invention will now be described with reference to the following examples:

EXAMPLE 1

The absorbency of the dressing described in FIG. 1 was measured against the absorbency of a dressing used in the Jubilee method referenced above. The absorbencies of the dressings were measured using the method described in BS EN 13726-1:2002 Test Methods for Primary Wound Dressings—Part 1: Aspects of absorbency.

The results are shown below:

|  | Control, Jubilee method (4 layers of Aquacel and DuoDerm Extra Thin) | Dressing of FIG. 1 |
| --- | --- | --- |
| Fluid absorbed by dressing (g/10 cm$^2$) (24 hr) | 6.3 (5.9-6.8) | 6.9 (6.8-7.0) |
| Fluid handling capacity (g/10 cm$^2$) (24 hr) | 6.6 (6.2-7.2) | 7.4 (7.3-7.5) |

These results show that the dressing according to the invention with a gathered absorbent layer has an absorbency and fluid handling capacity equivalent to that of a dressing using four layers of the same absorbent material.

EXAMPLE 2

The resilience of the dressing of FIG. 1 was measured by hydrating the dressing with 30 ml of solution A which was coloured using blue food dye. Masking tape was adhered to the short ends of the dressing and the dressing fixed in the grips of a Zwick Universal Testing Machine. The distance between the grips was extended by 20% and the Zwick was set to run a cyclic test with a pause at maximum extension of 15 seconds and a pause at recovery of 60 seconds. The number of cycles was 1000 with a speed of travel of 250 mm per minute. After testing no breakdown of the dressing was seen. The dressing remained integral and retained all of the solution A added at the beginning of the test. The force required to extend a 25 cm dressing length was 10.76 N. The stretch as a percentage of the original dressing length was 20%.

These results suggest that the dressing may enable increased or easier limb movement during patient rehabilitation.

The invention claimed is:

1. A wound dressing comprising a nonwoven absorbent layer, the absorbent layer comprising two or more layers of fabric, wherein the two or more layers of fabric comprise gel-forming fibers, are layered together to substantially overlap and are gathered in a longitudinal direction by stitching through the two or more layers of fabric using one or more resilient threads or yarns and an inelastic thread or yarn, wherein the resilient and inelastic threads or yarns gather the two or more layers of fabric so that the two or more layers of fabric in use are configured to;
   (a) maintain close conformability with a wound during movement and
   (b) elongate by 35% to 85% and then recover.

2. The wound dressing as claimed in claim 1 further comprising an adhesive layer overlying the absorbent layer on a surface furthest from the wound in use and extending beyond the periphery of the absorbent layer so as to adhere the dressing to the skin surrounding the wound.

3. The wound dressing as claimed in claim 1 characterized in that the resilient thread or yarn is woven in between the inelastic thread or yarn stitches and between the two or more layer of fabric to gather the two or more layers of fabric.

4. A method of manufacturing a wound dressing for use on post-surgical wounds characterized in that the method comprises the steps of:
   (i) forming a nonwoven absorbent layer comprising two or more layers of fabric, wherein the two or more layers of fabric comprise gel forming fibers and are layered together to substantially overlap;
   (ii) gathering the two or more layers of fabric by stitching through the two or more layers of fabric with a resilient thread or yarn and an inelastic thread or yarn, wherein the resilient and inelastic threads or yarns gather the two or more layers of fabric so that the two or more layers of fabric in use are configured to:
      (a) maintain close conformability with a wound during movement, and
      (b) elongate by 35% to 85% and then recover;
   (iii) overlying the absorbent layer with an adhesive layer on a surface furthest from the wound in use and extending beyond the periphery of the absorbent layer so as to adhere the dressing to the skin.

5. The method as claimed in claim 4 characterized in that the two or more layers of fabric are formed from nonwoven fabrics.

6. The method as claimed in claim 5 characterized in that the method comprises the further step of simultaneously weaving the resilient thread or yarn about the stitches of inelastic thread or yarn.

7. The method as claimed in claim 6 characterized in that the resilient thread or yarn is woven about the stitches of inelastic thread or yarn and carried at the center of the two or more layers of fabric.

8. The method as claimed in claim 6 characterized in that the resilient thread or yarn is stitched about the stitches of inelastic thread or yarn.

* * * * *